US012108791B2

(12) United States Patent
Fringeli

(10) Patent No.: US 12,108,791 B2
(45) Date of Patent: Oct. 8, 2024

(54) AEROSOL-GENERATING DEVICE COMPRISING A COVER ELEMENT

(71) Applicant: Philip Morris Products S.A., Neuchatel (CH)

(72) Inventor: Jean-Luc Fringeli, Singapore (SG)

(73) Assignee: Philip Morris Products S.A., Neuchatel (CH)

( * ) Notice: Subject to any disclaimer, the term of this patent is extended or adjusted under 35 U.S.C. 154(b) by 1045 days.

(21) Appl. No.: 16/970,784

(22) PCT Filed: Mar. 8, 2019

(86) PCT No.: PCT/EP2019/055916
§ 371 (c)(1),
(2) Date: Aug. 18, 2020

(87) PCT Pub. No.: WO2019/170893
PCT Pub. Date: Sep. 12, 2019

(65) Prior Publication Data
US 2021/0093007 A1 Apr. 1, 2021

(30) Foreign Application Priority Data
Mar. 9, 2018 (EP) .................................... 18161069

(51) Int. Cl.
*A24F 40/40* (2020.01)
*A24F 40/46* (2020.01)
(Continued)

(52) U.S. Cl.
CPC .............. *A24F 40/40* (2020.01); *A24F 40/46* (2020.01); *A24F 40/51* (2020.01); *A24F 40/85* (2020.01);
(Continued)

(58) Field of Classification Search
CPC .......... A24F 40/40; A24F 40/46; A24F 40/51; A24F 40/85; A24F 40/20; A24F 40/50;
(Continued)

(56) References Cited

U.S. PATENT DOCUMENTS 5,934,289 A    8/1999  Watkins et al.
9,826,780 B2  11/2017  Krietzman
(Continued)

FOREIGN PATENT DOCUMENTS

CN    205695707 U  * 11/2016
CN    107752130 A    3/2018
(Continued)

OTHER PUBLICATIONS

International Search Report issued on May 20, 2019 in PCT/EP2019/055916 filed on Mar. 8, 2019 (5 pages).
(Continued)

*Primary Examiner* — Justin M Kratt
(74) *Attorney, Agent, or Firm* — Oblon, McClelland, Maier & Neustadt, L.L.P.

(57) ABSTRACT

An aerosol-generating device is provided, including: a housing including an end wall; a cavity configured to removably receive an aerosol-generating article; an aperture at least partially defined by the housing and extending through a first portion of the end wall, the aperture being disposed at an end of the cavity and configured for insertion of the article into the cavity through the aperture; and a cover configured for rotational movement with respect to the housing and being rotatable between a closed position entirely covering the aperture and an open position in which the aperture is entirely uncovered and the cover overlies a second portion of the end wall, the cover including a cover portion and a shaft portion extending orthogonally from the cover portion, the cover portion entirely covering the aperture when the
(Continued)

cover is in the closed position, and the shaft portion being received within the housing.

11 Claims, 5 Drawing Sheets

(51) Int. Cl.
| | |
|---|---|
| *A24F 40/51* | (2020.01) |
| *A24F 40/85* | (2020.01) |
| *H05B 3/10* | (2006.01) |
| *H05B 3/40* | (2006.01) |
| *A24F 40/20* | (2020.01) |
| *A24F 40/50* | (2020.01) |
| *A61M 11/04* | (2006.01) |
| *A61M 15/00* | (2006.01) |
| *H05B 3/36* | (2006.01) |
| *H05B 3/42* | (2006.01) |
| *H05B 3/44* | (2006.01) |
| *H05B 3/46* | (2006.01) |
| *H05B 3/48* | (2006.01) |
| *H05B 3/54* | (2006.01) |

(52) U.S. Cl.
CPC ............ *H05B 3/10* (2013.01); *H05B 3/40* (2013.01); *A24F 40/20* (2020.01); *A24F 40/50* (2020.01); *A61M 11/04* (2013.01); *A61M 11/041* (2013.01); *A61M 11/042* (2014.02); *A61M 15/0001* (2014.02); *A61M 15/0006* (2014.02); *H05B 3/36* (2013.01); *H05B 3/42* (2013.01); *H05B 3/44* (2013.01); *H05B 3/46* (2013.01); *H05B 3/48* (2013.01); *H05B 3/54* (2013.01)

(58) Field of Classification Search
CPC ... H05B 3/10; H05B 3/40; H05B 3/36; H05B 3/42; H05B 3/44; H05B 3/46; H05B 3/48; H05B 3/54; A61M 11/04; A61M 11/041; A61M 11/042; A61M 15/0001; A61M 15/0006
See application file for complete search history.

(56) References Cited

U.S. PATENT DOCUMENTS

| | | | |
|---|---|---|---|
| 2014/0305449 A1* | 10/2014 | Plojoux | A24F 40/46 |
| | | | 131/328 |
| 2016/0235122 A1 | 8/2016 | Krietzman | |
| 2016/0235123 A1 | 8/2016 | Krietzman | |
| 2017/0202268 A1* | 7/2017 | Li | F16J 15/022 |
| 2017/0304567 A1 | 10/2017 | Adelson | |
| 2019/0029322 A1 | 1/2019 | Krietzman | |

FOREIGN PATENT DOCUMENTS

| | | |
|---|---|---|
| EP | 0 951 219 A1 | 10/1999 |
| JP | 2002-514910 A | 5/2002 |
| JP | 2015-506170 A | 3/2015 |
| RU | 2 614 376 C2 | 3/2017 |
| WO | WO 98/17130 A1 | 4/1998 |
| WO | WO 2013/098395 A1 | 7/2013 |
| WO | WO 2016/023172 A1 | 2/2016 |
| WO | WO 2017/182976 A1 | 10/2017 |
| WO | WO 2017/194751 A1 | 11/2017 |
| WO | WO 2017/194763 A2 | 11/2017 |
| WO | WO 2019/170896 A1 | 9/2019 |
| WO | WO 2019/170901 A1 | 9/2019 |

OTHER PUBLICATIONS

Written Opinion of the International Search Authority issued on May 20, 2019 in PCT/EP2019/055916 filed on Mar. 8, 2019 (6 pages).

Combined Russian Office Action and Search report issued Jun. 16, 2022 in Russian Patent Application No. 2020132618 (with unedited computer generated English Translation), 15 pages.

Japanese Office Action issued Mar. 23, 2023 in Japanese Application 2020-544659, (with English translation), 7 pages.

Combined Chinese Office Action and Search Report issued Nov. 24, 2023 in Chinese Patent Application No. 201980012561.4 (with English Translation), 15 pages.

* cited by examiner

AEROSOL-GENERATING DEVICE COMPRISING A COVER ELEMENT

CROSS-REFERENCE TO RELATED APPLICATIONS

This application is a U.S. national stage application of PCT/EP2019/055916, filed on Mar. 8, 2019, which is based upon and claims the benefit of priority under 35 U.S.C. § 119 to European patent application no. 18161069.2, filed Mar. 9, 2018, the entire contents of each of which are incorporated herein by reference.

TECHNICAL FIELD

The present invention relates to an aerosol-generating device comprising a rotatable cover element. The present invention also relates to an aerosol-generating system comprising the aerosol-generating device and an aerosol-generating article.

DESCRIPTION OF THE RELATED ART

One type of aerosol-generating system is an electrically operated smoking system. Known handheld electrically operated smoking systems typically comprise an aerosol-generating device comprising a battery, control electronics and an electric heater for heating an aerosol-generating article designed specifically for use with the aerosol-generating device. In some examples, the aerosol-generating article comprises an aerosol-forming substrate, such as a tobacco rod or a tobacco plug, and the heater contained within the aerosol-generating device is inserted into or located around the aerosol-forming substrate when the aerosol-generating article is inserted into the aerosol-generating device. In an alternative electrically operated smoking system, the aerosol-generating article may comprise a capsule containing an aerosol-forming substrate, such as loose tobacco.

In known electrically operated smoking systems the aerosol-generating article may be received within a cavity in the aerosol-generating device. Some aerosol-generating devices may comprise a sliding cover that a user may slide over an opening of the cavity when the aerosol-generating device is not being used. However, the sliding cover may be difficult for a user to operate with one hand. In other words, a user may find it difficult to hold the aerosol-generating device with one hand and open or close the cover with the same hand.

It would be desirable to provide an aerosol-generating device comprising a cover element that facilitates simple operation of the cover element.

SUMMARY

According to a first aspect of the present invention there is provided an aerosol-generating device comprising a housing, a cavity for receiving an aerosol-generating article, and an aperture at least partially defined by the housing. The aperture is positioned at an end of the cavity for insertion of an aerosol-generating article into the cavity through the aperture. The aerosol-generating device also comprises a cover element arranged for rotational movement with respect to the housing, wherein the cover element is rotatable between a closed position in which the cover element at least partially covers the aperture and an open position in which the aperture is at least partially uncovered.

According to a second aspect of the present invention there is provided an aerosol-generating system comprising an aerosol-generating device according to the first aspect of the present invention in accordance with any of the embodiments described herein. The aerosol-generating system also comprises an aerosol-generating article comprising an aerosol-forming substrate.

BRIEF DESCRIPTION OF THE DRAWINGS

Embodiments of the invention are further described, by way of example only, with reference to the accompanying drawings, in which.

DETAILED DESCRIPTION

Figure 1:
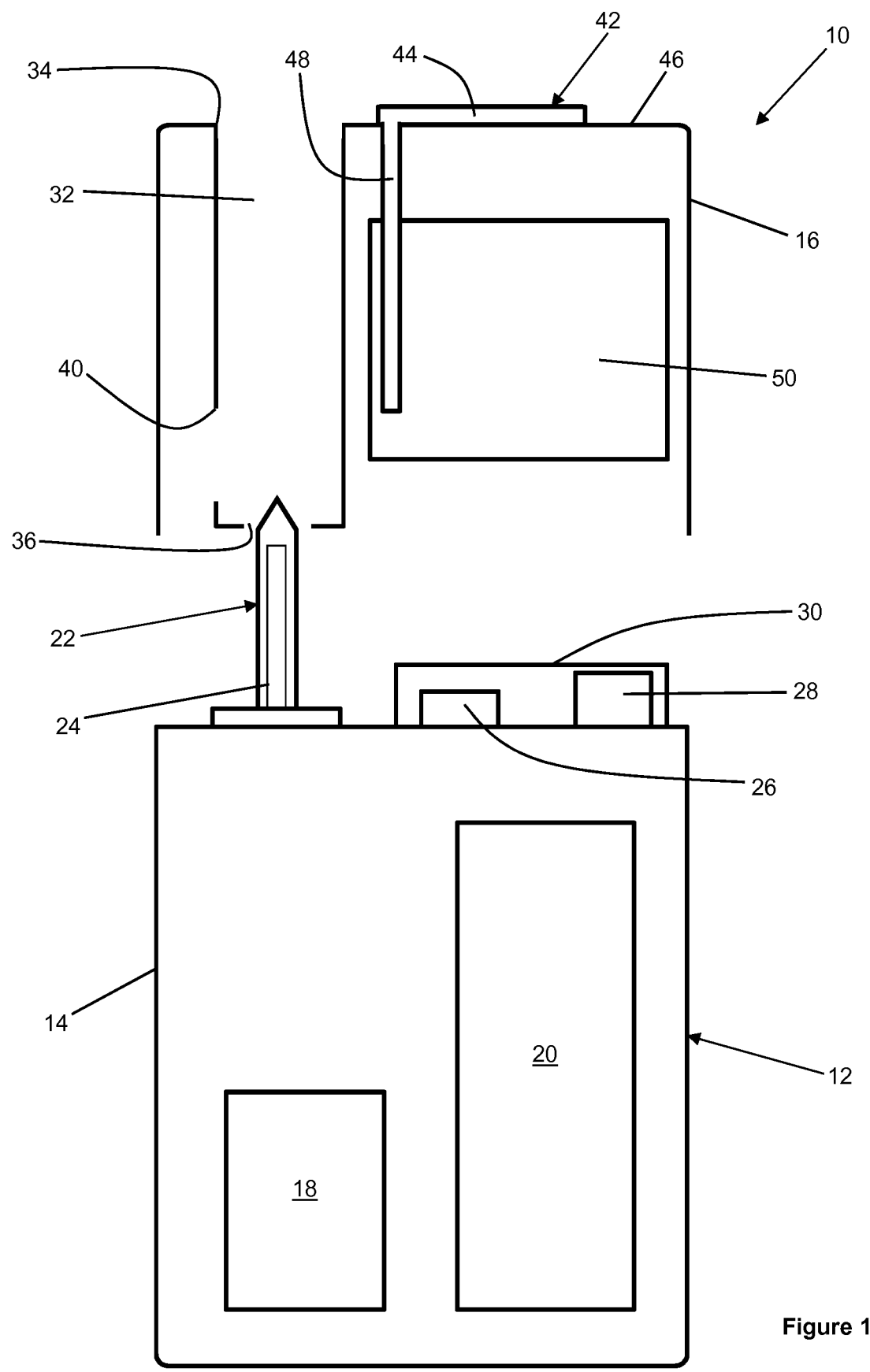
FIG. 1 shows a cross-sectional view of an aerosol-generating device according to an embodiment of the present invention.

Aerosol-generating devices according to the present invention comprise a rotatable cover element for selectively covering an aperture through which an aerosol-generating article may be inserted into a cavity. Advantageously, the present inventors have recognised that a rotatable cover element may be easier for a user to operate than a sliding cover element. For example, when a user is holding the aerosol-generating device with a hand, a rotational movement of the thumb of the same hand may be a more natural movement than a sliding motion. Therefore, advantageously, aerosol-generating devices according to the present invention facilitate holding the aerosol-generating device and operating the cover element with a single hand. Advantageously, holding the aerosol-generating device and operating the cover element with a single hand facilitates insertion of an aerosol-generating article into the cavity. For example, a user may hold the aerosol-generating device in one hand and operate the cover element with the same hand, and at the same time use the remaining hand to hold an aerosol-generating article and insert the aerosol-generating article into the cavity. Known devices require a user to use both hands to hold the aerosol-generating device and operate a cover element before the user can pick up and insert an article into the device.

Preferably, the cover element is arranged so that, when the cover element is in the closed position, the cover element covers at least about 50 percent of the aperture, more preferably at least about 60 percent of the aperture, more preferably at least about 70 percent of the aperture, more preferably at least about 80 percent of the aperture, more preferably at least about 90 percent of the aperture, more preferably at least about 95 percent of the aperture.

Preferably, the cover element is arranged so that the cover element entirely covers the aperture when the cover element is in the closed position. In other words, preferably the cover element is arranged so that the cover element covers 100 percent of the aperture when the cover element is in the closed position. Advantageously, arranging the cover element to entirely cover the aperture when the cover element is in the closed position may prevent the insertion of foreign objects into the cavity when the aerosol-generating device is not being used.

Preferably, the cover element is arranged so that the cover element covers less than about 5 percent of the aperture when the cover element is on the open position.

Preferably, the cover element is arranged so that the aperture is entirely uncovered when the cover element is in the open position. In other words, preferably the cover element is arranged so that the cover element covers none of the aperture when the cover element is in the open position. Advantageously, arranging the cover element so that the aperture is entirely uncovered when the cover element is in the open position facilitates insertion of an aerosol-generating article into the cavity.

Preferably, the cover element comprises a cover portion and a shaft portion extending from the cover portion, wherein the cover portion is arranged to at least partially cover the aperture when the cover element is in the closed position, and wherein the shaft portion is received within the housing. Advantageously, the shaft portion may facilitate rotation of the cover element between the closed position and the open position.

The cover portion and the shaft portion may be formed separately and attached to each other. For example, the cover portion and the shaft portion may be attached to each other using at least one of an adhesive, an interference fit, and a weld.

The cover portion and the shaft portion may be integrally formed. For example, the cover portion and the shaft portion may be formed as a single piece using a molding process.

The cover portion may be substantially planar. The cover portion may be disc-shaped.

Preferably, the shaft portion extends orthogonally with respect to the cover portion.

The cover element may be manually moveable from the closed position to the open position.

The cover element may be manually moveably from the open position to the closed position.

Preferably, the aerosol-generating device comprises a biasing mechanism arranged to bias the cover element away from the open position and towards the closed position.

Advantageously, the biasing mechanism may eliminate the need for a user to manually move the cover element into the closed position. Advantageously, the biasing mechanism may reduce the risk of accidental movement of the cover element away from the closed position and towards the open position. Advantageously, during use, the biasing mechanism may bias the cover element against and aerosol-generating article received within the cavity, which may inhibit movement of the aerosol-generating article during use.

The biasing mechanism may comprise a torsion spring. Advantageously, a torsion spring may be particularly suitable for providing a rotational biasing force to bias the rotatable cover element away from the open position and towards the closed position. A rotational biasing force may also be referred to as torque.

In embodiments in which the cover element comprises a shaft portion, the torsion spring may be arranged to act directly on the shaft portion. For example, the cover element may comprise a tab extending from the shaft portion and arranged to engage an end of the torsion spring.

The biasing mechanism may comprise a first gear connected to the shaft portion of the cover element and a second gear connected to the torsion spring, wherein the first gear is engaged with the second gear to translate torque from the torsion spring to the shaft portion.

The first gear and the shaft portion may be formed separately and attached to each other. For example, the first gear and the shaft portion may be attached to each other using at least one of an adhesive, an interference fit, and a weld.

The first gear and the shaft portion may be integrally formed. For example, the first gear and the shaft portion may be formed as a single piece using a molding process.

The biasing mechanism may comprise a spring holder in which the torsion spring is at least partially received, wherein at least a portion of an outer surface of the spring holder forms the second gear.

The torsion spring may be retained in the spring holder by an interference fit.

The biasing mechanism may comprise a cap, wherein the torsion spring is positioned between the spring holder and the cap. Advantageously, the cap may retain the torsion spring within the spring holder.

Preferably, the spring holder is rotatable with respect to the cap. Preferably, the torsion spring comprises a first end engaged with the cap and a second end engaged with the spring holder.

Preferably, the biasing mechanism comprises a spindle extending from the cap, wherein the torsion spring extends around the spindle. Preferably, the spring holder is rotatable about the spindle. Advantageously, the spindle may facilitate correct positioning of the torsion spring during assembly of the biasing mechanism.

The spindle and the cap may be formed separately and attached to each other. For example, the spindle and the cap may be attached to each other using at least one of an adhesive, an interference fit, and a weld.

The spindle and the cap may be integrally formed. For example, the spindle and the cap may be formed as a single piece using a molding process.

The biasing mechanism may comprise a chassis on which at least one of the shaft portion, the torsion spring, the first gear, the second gear, the spring holder, the cap, and the spindle is received. Preferably, the cap is connected to the chassis to retain the spring holder and the torsion spring between the cap and the chassis. Preferably, the cap is connected to the chassis by an interference fit.

The aerosol-generating device may comprise a first detent arranged to retain the cover element in the open position. Advantageously, the first detent increases the force required to rotate the cover element out of the open position. Therefore, the first detent may be particularly advantageous in embodiments in which the aerosol-generating device comprises a biasing mechanism. For example, the biasing force provided by the biasing mechanism may be insufficient to move the cover element out of the open position when a portion of the aerosol-generating device is engage with the detent. Therefore, the aerosol-generating device may require additional force from the user to overcome the first detent, at which point the biasing mechanism is sufficient to continue rotation of the cover element into the closed position.

The first detent may be arranged to engage a protrusion on at least one of the cover element, the cover portion, the shaft portion, the first gear, the second gear, and the spring holder. The first detent may be formed by at least one of the housing, the biasing mechanism cap and the biasing mechanism chassis.

The aerosol-generating device may comprise a second detent arranged to retain the cover element in the closed position. Advantageously, the second detent increases the force required to rotate the cover element out of the closed position. Therefore, advantageously, the second detent may reduce the risk of accidental opening of the cover element.

The second detent may be arranged to engage a protrusion on at least one of the cover element, the cover portion, the shaft portion, the first gear, the second gear, and the spring holder. The second detent may be formed by at least one of the housing, the biasing mechanism cap and the biasing mechanism chassis.

The aerosol-generating device may comprise the first detent, the second detent, or both the first detent and the second detent.

In embodiments in which the aerosol-generating device comprises the first detent and the second detent, the aerosol-generating device may comprise a common detent that functions as both the first detent and the second detent. The common detent may be arranged to engage a first protrusion on at least one of the cover element, the cover portion, the shaft portion, the first gear, the second gear, and the spring holder to retain the cover element in the open position. The common detent may be arranged to engage a second protrusion on at least one of the cover element, the cover portion, the shaft portion, the first gear, the second gear, and the spring holder to retain the cover element in the closed position.

In embodiments in which the aerosol-generating device comprises separate first and second detents, at least one of the cover element, the cover portion, the shaft portion, the first gear, the second gear, and the spring holder may define a common protrusion. Preferably, the common protrusion is arranged to engage the first detent when the cover element is in the open position. Preferably, the common detent is arranged to engage the second detent when the cover element is in the closed position.

The aerosol-generating device may comprise a first mechanical stop arranged to prevent rotation of the cover element beyond the closed position when the cover element is rotated from the open position to the closed position.

The first mechanical stop may be arranged to engage at least one of the cover element, the cover portion, the shaft portion, the first gear, the second gear, and the spring holder. The first mechanical stop may be formed by at least one of the housing, the biasing mechanism cap and the biasing mechanism chassis.

The aerosol-generating device may comprise a second mechanical stop arranged to prevent rotation of the cover element beyond the open position when the cover element is rotated from the closed position to the open position.

The second mechanical stop may be arranged to engage at least one of the cover element, the cover portion, the shaft portion, the first gear, the second gear, and the spring holder. The second mechanical stop may be formed by at least one of the housing, the biasing mechanism cap and the biasing mechanism chassis.

The aerosol-generating device may comprise the first mechanical stop, the second mechanical stop, or both the first mechanical stop and the second mechanical stop.

In embodiments in which the aerosol-generating device comprises the first mechanical stop and the second mechanical stop, the aerosol-generating device may comprise a common mechanical stop that functions as both the first mechanical stop and the second mechanical stop. The common mechanical stop may be arranged to engage a first portion of at least one of the cover element, the cover portion, the shaft portion, the first gear, the second gear, and the spring holder to retain the cover element in the open position. The common mechanical stop may be arranged to engage a second portion of at least one of the cover element, the cover portion, the shaft portion, the first gear, the second gear, and the spring holder to retain the cover element in the closed position.

The housing may comprise an end wall, wherein the aperture extends through a first portion of the end wall. Preferably, the cover element is arranged to overlie a second portion of the end wall when the cover portion is in the open position. Advantageously, arranging the cover element to overlie a second portion of the end wall when the cover portion is in the open position may reduce the risk of damage to the cover element when the aerosol-generating device is being used with the cover element in the open position.

In embodiments in which the cover element comprises a shaft portion, preferably the shaft portion extends through an opening in the housing end wall. Preferably, the opening is positioned on a central portion of the end wall, wherein the central portion is positioned between the first portion of the end wall and the second portion of the end wall.

The aperture may define a first end of the cavity, wherein the cavity comprises a second end opposite the first end. Preferably, the cavity has a maximum length between the first end of the cavity and the second end of the cavity of between about 20 millimetres and about 70 millimetres. Advantageously, a cavity having a maximum length of greater than about 20 millimetres may allow the cavity to receive a sufficient portion of an aerosol-generating article so facilitate retention of the aerosol-generating article within the cavity during use. Advantageously, a cavity having a maximum length of less than about 70 millimetres may allow a portion of an aerosol-generating article to extend out of the aerosol-generating device when the aerosol-generating article is fully inserted into the cavity. Advantageously, a portion of an aerosol-generating article extending out of the aerosol-generating device allows a user to puff directly on the aerosol-generating article. Advantageously, puffing directly on an aerosol-generating article may simulate puffing on a conventional cigarette.

The cavity may have a maximum length of between about 20 millimetres and about 40 millimetres. The cavity may have a maximum length of between about 30 millimetres and about 70 millimetres. The cavity may have a maximum length of between about 30 millimetres and about 60 millimetres.

Preferably, the aerosol-generating device comprises a heater arranged to heat an aerosol-generating article when the aerosol-generating article is received within the cavity.

The heater may comprise an electrical heater.

The electrical heater may be positioned outside the cavity.

The electrical heater may be positioned within the cavity.

The electrical heater may be arranged to extend around an outer surface of an aerosol-generating article received within the cavity. The electrical heater may have a tubular shape. The electrical heater may comprise an electrically insulating substrate and at least one resistive heating track on the electrically insulating substrate. The electrically insulating substrate may comprise a flexible sheet. Advantageously, a flexible sheet may facilitate manufacturing the electrical heater in a flat state and subsequently deforming the flexible sheet into a desired shape. For example, the electrical heater may be formed in a flat state and then rolled into a tubular shape. The electrically insulating substrate may comprise a polyimide film. The at least one resistive heating track may comprise at least one metal. The at least one resistive heating track may comprise a metal. The at least one resistive heating track may comprise a metal alloy. Examples of suitable metals include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys.

The at least one resistive heating track may define a plurality of heating zones.

The at least one resistive heating track may comprise a plurality of heating tracks. The plurality of heating tracks may define a plurality of heating zones.

The at least one resistive heating track may comprise a single heating track comprising a plurality of portions, wherein each portion defines a heating zone.

Advantageously, at least some of the heating zones may be heated to different temperature during use. Advantageously, at least some of the heating zones may be heated at different times during use. Each heating zone may be defined by a single resistive heating track. Each heating zone may be defined by a plurality of resistive heating tracks.

In embodiments in which the electrical heater is arranged to extend around an outer surface of an aerosol-generating article received within the cavity, advantageously the cavity may have a maximum length of between about 30 millimetres and about 70 millimetres. The cavity may have a maximum length of between about 30 millimetres and about 60 millimetres.

The electrical heater may be coil-shaped. The electrical heater may be configured to heat a fluid transport structure. The aerosol-generating device may comprise a fluid transport structure, wherein the electrical heater is arranged to heat the fluid transport structure. The fluid transport structure may comprise a wick. The electrical heater may be coil-shaped, wherein the electrical heater is coiled around the fluid transport structure.

The electrical heater may extend into the cavity. The electrical heater may be arranged to be received within an aerosol-generating article when the aerosol-generating article is inserted into the cavity. The electrical heater may be an elongate electrical heater. The elongate electrical heater may comprise a distal end arranged to be received within an aerosol-generating article and a proximal end opposite the distal end. The electrical heater may be blade-shaped. The electrical heater may be pin-shaped. The electrical heater may be cone-shaped.

The elongate electrical heater may comprise at least one resistive heating track. The at least one resistive heating track may be surrounded by an electrically insulating substrate. The at least one resistive heating track may be embedded within an electrically insulating substrate. The electrically insulating substrate may comprise a ceramic. The electrically insulating substrate may be received within a tubular shell. The tubular shell may comprise at least one metal.

In embodiments in which the electrical heater is an elongate electrical heater, advantageously the cavity may have a maximum length of between about 20 millimetres and about 40 millimetres.

The electrical heater may comprise an inductive heating element. During use, the inductive heating element inductively heats a susceptor material to heat an aerosol-generating article received within the cavity. The susceptor material may form part of the aerosol-generating device. The susceptor material may form part of the aerosol-generating article.

The electrical heater may comprise a resistive heating element. During use, an electrical current is supplied to the resistive heating element to generate heat by resistive heating.

Suitable materials for forming the resistive heating element include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys.

In some embodiments, the resistive heating element comprises one or more stamped portions of electrically resistive material, such as stainless steel. Alternatively, the resistive heating element may comprise a heating wire or filament, for example a Ni—Cr (Nickel-Chromium), platinum, tungsten or alloy wire.

The electrical heater may comprise an electrically insulating substrate, wherein the resistive heating element is provided on the electrically insulating substrate. The electrically insulating substrate may be a ceramic material such as Zirconia or Alumina. Preferably, the electrically insulating substrate has a thermal conductivity of less than or equal to about 2 Watts per metre Kelvin.

Preferably, the aerosol-generating device comprises a power supply and a controller arranged to supply power from the power supply to the electrical heater during use of the aerosol-generating device.

Preferably, the controller is arranged to supply power from the power supply to the electrical heater according to a predetermined heating cycle when the aerosol-generating device is used to heat an aerosol-generating article received within the cavity.

In embodiments in which the electrical heater comprises a resistive heating element, the controller may be arranged to supply power from the power supply to the resistive heating element according to a predetermined pyrolysis cycle to clean the electrical heater when there is not an aerosol-generating article received within the cavity. The pyrolysis cycle may clean the electrical heater by pyrolysis of residue remaining on the electrical heater after use of the aerosol-generating device to heat one or more aerosol-generating articles. Typically, the maximum temperature to which the electrical heater is heated during a pyrolysis cycle is higher than the maximum temperature to which the electrical heater is heated during a heating cycle to heat an aerosol-generating article. Typically, the total duration of a pyrolysis cycle is shorter than the total duration of a heating cycle.

The power supply may be a DC voltage source. In preferred embodiments, the power supply is a battery. For example, the power supply may be a nickel-metal hydride battery, a nickel cadmium battery, or a lithium based battery, for example a lithium-cobalt, a lithium-iron-phosphate or a lithium-polymer battery. The power supply may alternatively be another form of charge storage device such as a capacitor. The power supply may require recharging and may have a capacity that allows for the storage of enough energy for use of the aerosol-generating device with one or more aerosol-generating articles.

Preferably, the aerosol-generating device comprises at least one air inlet. Preferably, the at least one air inlet is in fluid communication with an upstream end of the cavity. In embodiments in which the aerosol-generating device comprises an elongate electrical heater, preferably the elongate electrical heater extends into the cavity from the upstream end of the cavity.

The aerosol-generating device may comprise a sensor to detect air flow indicative of a user taking a puff. The air flow sensor may be an electro-mechanical device. The air flow sensor may be any of: a mechanical device, an optical device, an opto-mechanical device and a micro electro-mechanical systems (MEMS) based sensor. The aerosol-generating device may comprise a manually operable switch for a user to initiate a puff.

The aerosol-generating device may comprise a temperature sensor. The temperature sensor may be mounted on the printed circuit board. In embodiments in which the aerosol-generating device comprises an electrical heater, the temperature sensor may be mounted on the electrical heater. In embodiments in which the electrical heater comprises an electrically insulating substrate, the temperature sensor may be mounted on the electrically insulating substrate. In embodiments in which the electrical heater is an elongate electrical heater, the temperature sensor may be mounted on the distal end of the elongate electrical heater.

The temperature sensor may detect the temperature of the electrical heater or the temperature of an aerosol-generating article received within the cavity. The temperature sensor may be a thermistor. The temperature sensor may be a thermocouple. The temperature sensor may comprise a circuit configured to measure the resistivity of the electrical heater and derive a temperature of the electrical heater by comparing the measured resistivity to a calibrated curve of resistivity against temperature.

Advantageously, deriving the temperature of the electrical heater may facilitate control of the temperature to which the electrical heater is heated during use. The controller may be configured to adjust the supply of power to the electrical heater in response to a change in the measured resistivity of the electrical heater.

Advantageously, deriving the temperature of the electrical heater may facilitate puff detection. For example, a measured drop in the temperature of the electrical heater may correspond to a user puffing or drawing on the aerosol-generating device.

Preferably, the aerosol-generating device comprises an indicator for indicating when the electrical heater is activated. The indicator may comprise a light, activated when the electrical heater is activated.

The aerosol-generating device may comprise at least one of an external plug or socket and at least one external electrical contact allowing the aerosol-generating device to be connected to another electrical device. For example, the aerosol-generating device may comprise a USB plug or a USB socket to allow connection of the aerosol-generating device to another USB enabled device. The USB plug or socket may allow connection of the aerosol-generating device to a USB charging device to charge a rechargeable power supply within the aerosol-generating device. The USB plug or socket may support the transfer of data to or from, or both to and from, the aerosol-generating device.

The aerosol-generating device may be connectable to a computer to transfer data to the aerosol-generating device, such as new heating profiles for new aerosol-generating articles.

In those embodiments in which the aerosol-generating device comprises a USB plug or socket, the aerosol-generating device may further comprise a removable cover that covers the USB plug or socket when not in use. In embodiments in which the USB plug or socket is a USB plug, the USB plug may additionally or alternatively be selectively retractable within the device.

As used herein, the term "aerosol-generating article" refers to an article comprising an aerosol-forming substrate that, when heated, releases volatile compounds that can form an aerosol.

The aerosol-forming substrate may comprise a plug of tobacco. The tobacco plug may comprise one or more of: powder, granules, pellets, shreds, spaghettis, strips or sheets containing one or more of: tobacco leaf, fragments of tobacco ribs, reconstituted tobacco, homogenised tobacco, extruded tobacco and expanded tobacco. Optionally, the tobacco plug may contain additional tobacco or non-tobacco volatile flavour compounds, to be released upon heating of the tobacco plug. Optionally, the tobacco plug may also contain capsules that, for example, include the additional tobacco or non-tobacco volatile flavour compounds. Such capsules may melt during heating of the tobacco plug. Alternatively, or in addition, such capsules may be crushed prior to, during, or after heating of the tobacco plug.

Where the tobacco plug comprises homogenised tobacco material, the homogenised tobacco material may be formed by agglomerating particulate tobacco. The homogenised tobacco material may be in the form of a sheet. The homogenised tobacco material may have an aerosol-former content of greater than 5 percent on a dry weight basis. The homogenised tobacco material may alternatively have an aerosol former content of between 5 percent and 30 percent by weight on a dry weight basis. Sheets of homogenised tobacco material may be formed by agglomerating particulate tobacco obtained by grinding or otherwise comminuting one or both of tobacco leaf lamina and tobacco leaf stems; alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco. Alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof. Sheets of homogenised tobacco material are preferably formed by a casting process of the type generally comprising casting a slurry comprising particulate tobacco and one or more binders onto a conveyor belt or other support surface, drying the cast slurry to form a sheet of homogenised tobacco material and removing the sheet of homogenised tobacco material from the support surface.

Preferably, the aerosol-generating article is sized so that, wherein the aerosol-generating article is fully inserted into the cavity of the aerosol-generating device, a portion of the aerosol-generating article extends out of the aerosol-generating device. Advantageously, a portion of the aerosol-generating article extending out of the aerosol-generating device allows a user to puff directly on the aerosol-generating article. Advantageously, puffing directly on an aerosol-generating article may simulate puffing on a conventional cigarette.

The aerosol-generating article may have a total length of between approximately 30 millimetres and approximately 100 millimetres. The aerosol-generating article may have an external diameter of between approximately 5 millimetres and approximately 13 millimetres.

The aerosol-generating article may comprise a mouthpiece positioned downstream of the tobacco plug. The mouthpiece may be located at a downstream end of the aerosol-generating article. The mouthpiece may be a cellulose acetate filter plug. Preferably, the mouthpiece is approximately 7 millimetres in length, but can have a length of between approximately 5 millimetres to approximately 10 millimetres.

The tobacco plug may have a length of approximately 10 millimetres. The tobacco plug may have a length of approximately 12 millimetres.

The diameter of the tobacco plug may be between approximately 5 millimetres and approximately 12 millimetres.

In a preferred embodiment, the aerosol-generating article has a total length of between approximately 40 millimetres and approximately 50 millimetres. Preferably, the aerosol-generating article has a total length of approximately 45 millimetres. Preferably, the aerosol-generating article has an external diameter of approximately 7.2 millimetres.

Figure 2:
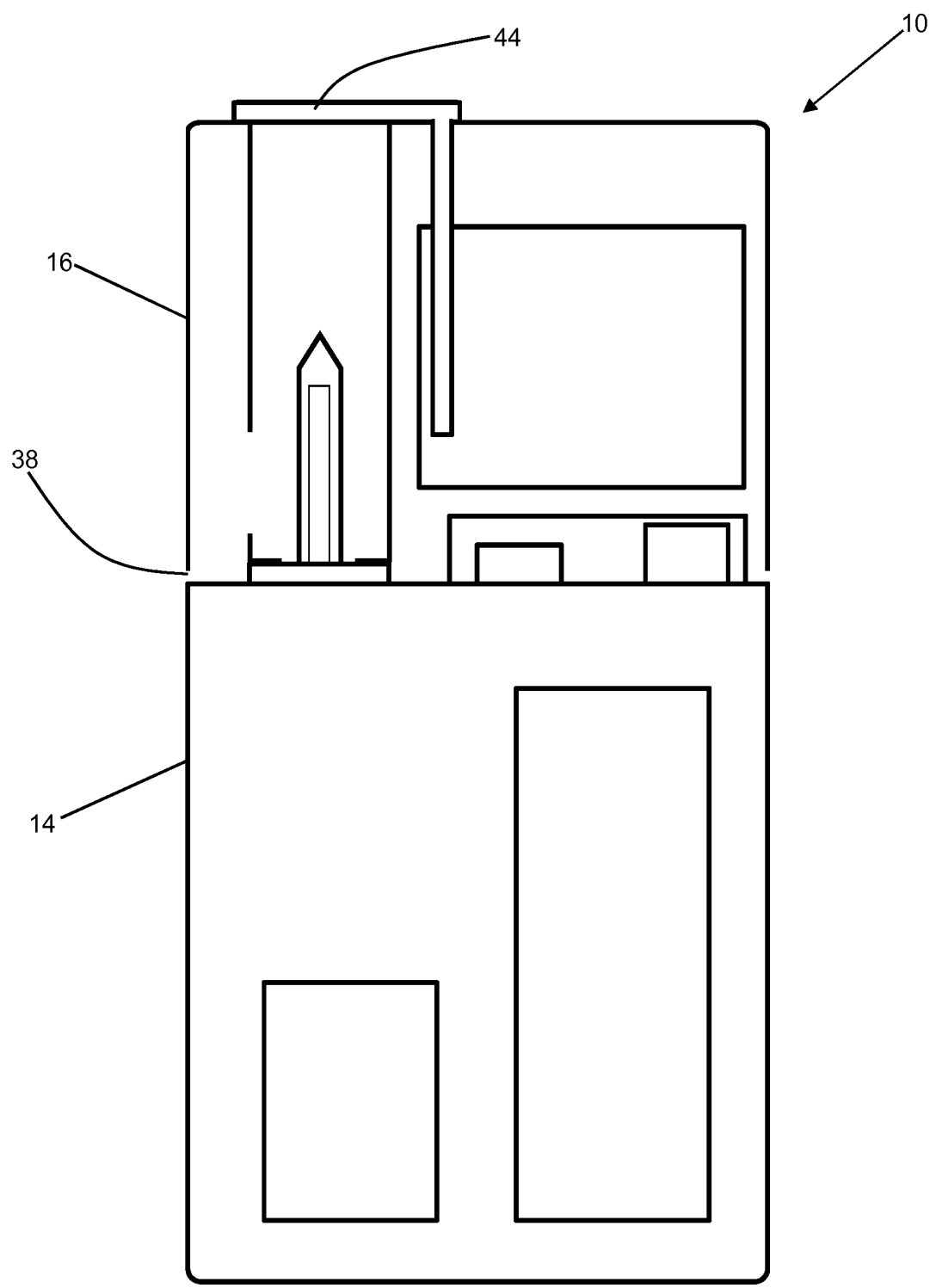
FIG. 2 shows a cross-sectional view of the aerosol-generating device of FIG. 1 with the second housing moved relative to the first housing.

FIGS. 1 and 2 show a cross-sectional view of an aerosol-generating device 10 according to an embodiment of the present invention. The aerosol-generating device 10 comprises a housing 12 comprising a first housing 14 and a second housing 16. The second housing 16 is slidable with respect to the first housing 14 between a compressed position shown in FIG. 2 and an expanded position shown in FIG. 1. The second housing 16 may also be detached from the first housing 14.

The aerosol-generating device 10 also comprises a controller 18 and a power supply 20 positioned within the first housing 14, and a heater 22 extending from an end of the first housing 14. The power supply 20 is an electrical power supply comprising a rechargeable battery. The heater 22 is an electrical heater comprising a resistive heating element 24. During use, the controller 18 supplies power from the power supply 20 to the resistive heating element 24 to resistively heat the heater 22.

Positioned on the first housing 14 next to the heater 22 are a sensor 26 and a first magnet 28. The sensor 26 is an optical sensor comprising a light transmitter and a light receiver. The light transmitter is an infrared light emitting diode and the light receiver is a photodiode. The photodiode is sensitive to infrared light transmitted from the infrared light emitting diode. An optical window 30 overlies the sensor 26, wherein the optical window is transparent to the infrared light transmitted from the infrared light emitting diode.

The second housing 16 defines a cavity 32 for receiving an aerosol-generating article and an aperture 34 positioned at an end of the cavity 32. When the second housing 16 is attached to the first housing 14, the heater 22 extends into the cavity 32 via a heater opening 36 defined by the second housing 16. An air inlet 38 is formed by a gap between the first housing 14 and the second housing 16. The air inlet 38 is in fluid communication with the cavity 32 via an airflow opening 40 defined by the second housing 16.

When an aerosol-generating article is received within the cavity 32, the aerosol-generating article and the aerosol-generating device 10 together form an aerosol-generating system. During use, the heater 22 heats the aerosol-generating article received within the cavity 32 to generate an aerosol. When a user draws on the aerosol-generating article, air is drawn into the aerosol-generating device 10 via the air inlet 38 and into the cavity 32 through the airflow opening 40. The air then flows through the aerosol-generating article to deliver the generated aerosol to the user.

Figure 3:
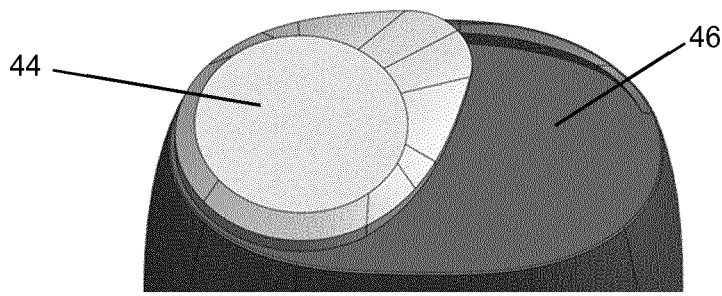
FIGS. 3 to 5 illustrate the rotational movement of the cover element of the aerosol-generating device of FIGS. 1 and 2.
Figure 4:
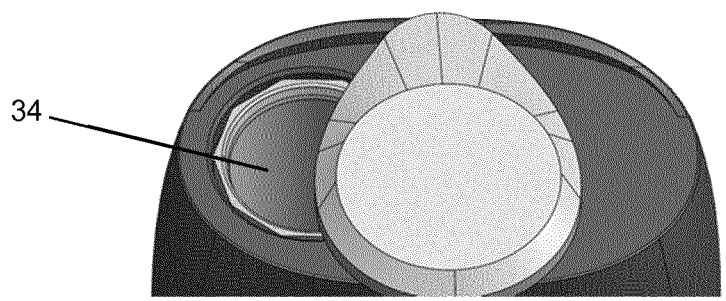
Figure 5:
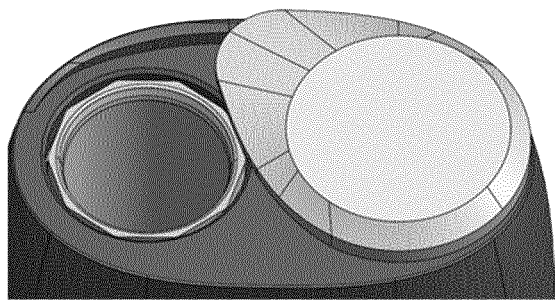

The aerosol-generating device 10 also comprises a cover element 42 comprising a cover portion 44 overlying an end wall 46 of the second housing 16 and a shaft portion 48 extending through the end wall 46. The cover element 42 is rotatable between a closed position in which the cover portion 44 covers the aperture 34 and an open position in which the cover portion 44 does not cover the aperture 34. The closed position is shown in FIG. 2 and the open position is shown in FIG. 1. FIGS. 3 to 5 illustrate the rotation of the cover element 42 from the closed position (FIG. 3) to the open position (FIG. 5).

Figure 6:
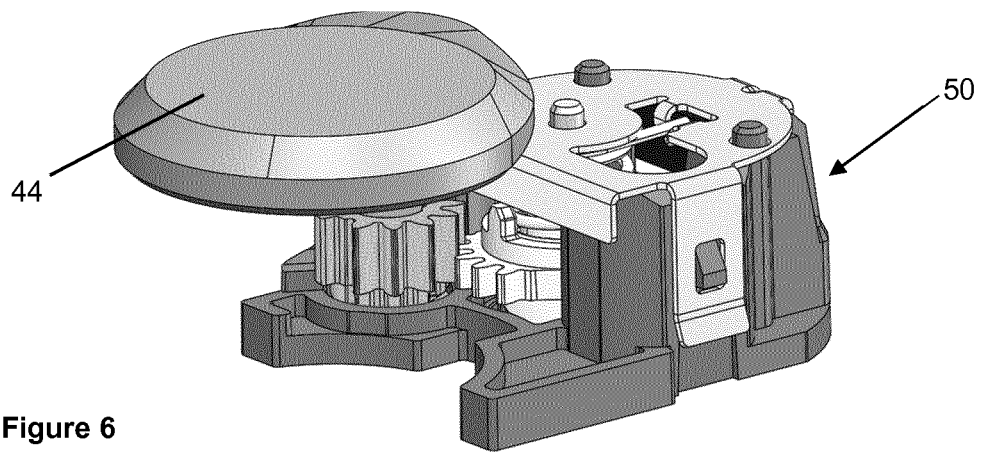
FIG. 6 shows a perspective view of the mechanical linkage of the aerosol-generating device of FIGS. 1 and 2.
Figure 7:
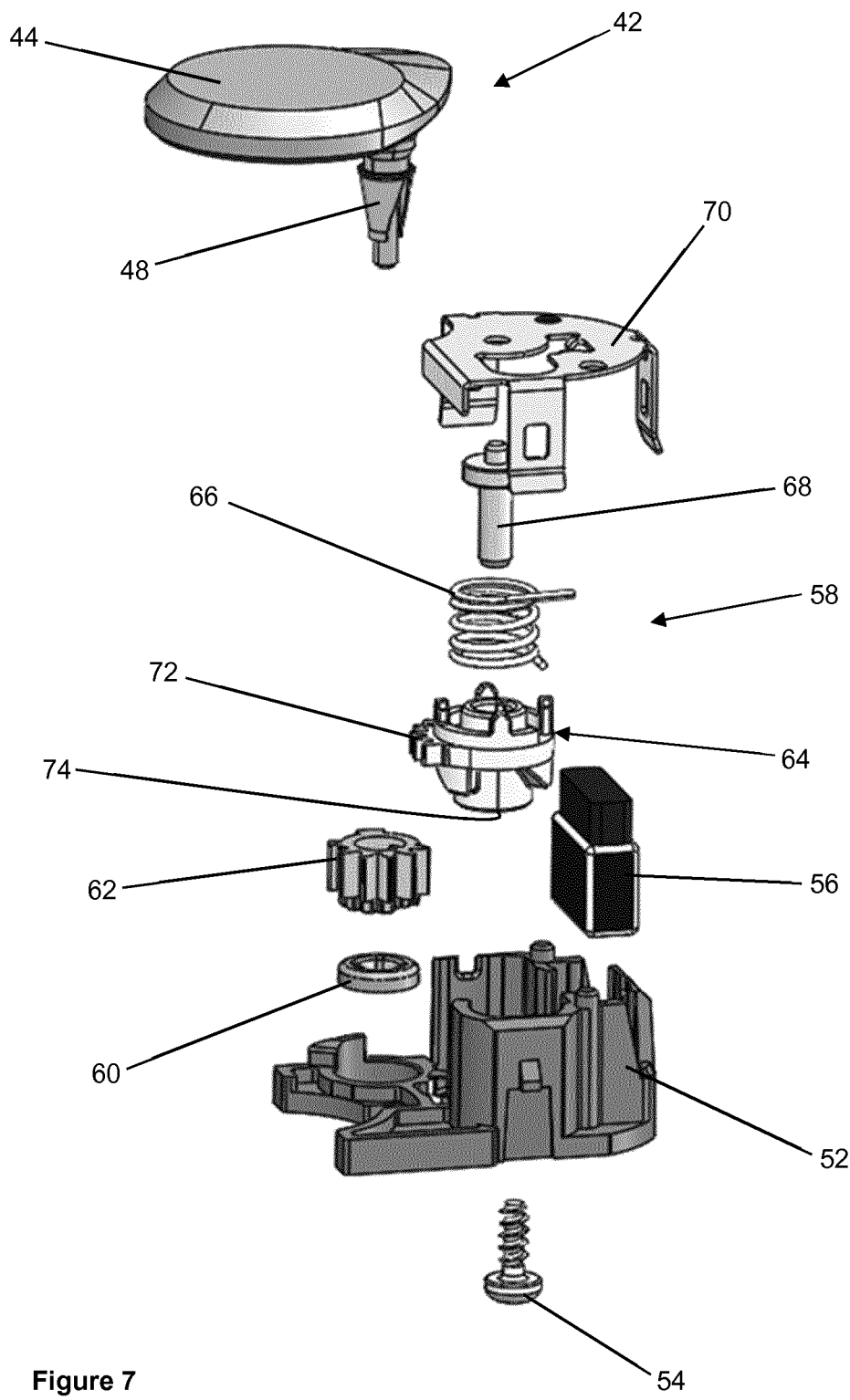
FIG. 7 shows an exploded view of the mechanical linkage of FIG. 6.

Positioned within the second housing 16 is a mechanical linkage 50 arranged to interact with the shaft portion 48 of the cover element 42. A perspective view of the mechanical linkage 50 is shown in FIG. 6 and an exploded view of the mechanical linkage 50 is shown in FIG. 7.

The mechanical linkage 50 comprises a chassis 52 attached to the second housing 16 by a screw 54. Mounted onto the chassis 52 is second magnet 56 arranged to interact with the first magnet 28 on the first housing 14. In particular, the first and second magnets 28, 56 are magnetically attracted to each other to facilitate attachment of the second housing 16 to the first housing 14.

Also mounted on the chassis 52 is a biasing mechanism 58 comprising a washer 60, a first gear 62, a spring holder 64, a torsion spring 66, a spindle 68 and a cap 70.

The washer 60 is formed from a low friction material to facilitate rotation of the first gear 62 on the chassis 52. The first gear 62 is connected to an end of the shaft portion 48 of the cover element 42 by an interference fit. Therefore, when the cover element 42 is rotated between the closed and open positions, the first gear 62 is also rotated.

An outer surface of the spring holder 64 forms a second gear 72 that is engaged with the first gear 62. The spring holder 64 is rotatably received within the chassis 52 and engages a cam surface formed on the chassis 52. Therefore, when the spring holder 64 rotates with respect to the cam surface, the spring holder 64 functions as a cam follower and moves up and down along the spindle 68. An indicator element 74 comprising an optically reflective aluminium layer is positioned on a bottom surface of the spring holder 64. When the spring holder 64 moves up and down along the spindle 68, the sensor 26 senses a change in distance between the sensor 26 and the indicator element 74. Based on the sensed distance between the sensor 26 and the indicator element 74, the sensor 26 provides a signal to the controller 18 indicative of whether the cover element 42 is in the closed position or the open position.

If the signal from the sensor 26 is indicative of the cover element 42 being in the closed position, it is assumed that an aerosol-generating article is not received within the cavity 32 and the controller 18 will not supply power from the power supply 20 to the heater 22 for heating an aerosol-generating article.

If the signal from the sensor 26 is indicative of the cover element 42 being in the open position, an aerosol-generating article may be received within the cavity 32 and the controller 18 may supply power from the power supply 20 to the heater 22 for heating an aerosol-generating article.

If the sensor 26 cannot detect the indicator element 74 it is assumed that the second housing 16 has been detached from the first housing 14. In this case, the sensor 26 provides a signal to the controller 18 indicative of the second housing 16 being detached from the first housing 14 and the controller 18 will prevent the supply of power to the heater 22.

A first end of the torsion spring 66 is engaged with the spring holder 64 and a second end of the torsion spring 66 is engaged with the cap 70. When a user rotates the cover element 42 from the closed position to the open position, the spring holder 64 rotates and loads the tension spring 66. When a user releases the cover element 42, the load on the tension spring 66 exerts a rotational force on the spring holder 64, which biases the cover element 42 from the open position towards the closed position.

Figure 8:
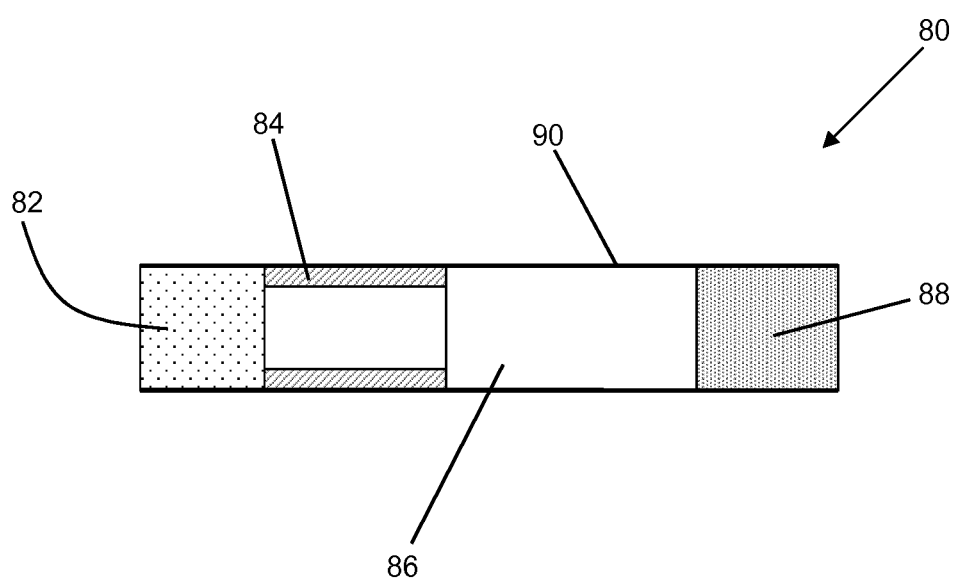
FIG. 8 shows a cross-sectional view of an aerosol-generating article for use with the aerosol-generating device of FIGS. 1 and 2.

FIG. 8 shows a cross-sectional view of an aerosol-generating article 80 for use with the aerosol-generating device 10. The aerosol-generating article 80 comprises an aerosol-forming substrate 82 in the form of a tobacco plug, a hollow acetate tube 84, a polymeric filter 86, a mouthpiece 88 and an outer wrapper 90. When the aerosol-generating article 80 is received within the cavity 32 of the aerosol-generating device 10, the heater 22 is received within the tobacco plug. During use, the heater 22 heats the tobacco plug to generate an aerosol.

The invention claimed is:

1. An aerosol-generating device, comprising:
   a housing comprising an end wall;
   a cavity configured to removably receive an aerosol-generating article;
   an aperture at least partially defined by the housing, wherein the aperture extends through a first portion of the end wall and wherein the aperture is disposed at an end of the cavity and configured for insertion of the aerosol-generating article into the cavity through the aperture;
   a cover element configured for rotational movement with respect to the housing, and being rotatable between a closed position in which the cover element entirely covers the aperture and an open position in which the aperture is entirely uncovered and the cover element overlies a second portion of the end wall, wherein the cover element comprises a cover portion and a shaft portion extending orthogonally from the cover portion, wherein the cover portion is configured to entirely cover the aperture when the cover element is in the closed position, and wherein the shaft portion is received within the housing;
   a heater arranged to heat the aerosol-generating article when the aerosol-generating article is received within the cavity, wherein the heater comprises an electrical heater positioned within the cavity, and wherein the electrical heater is arranged to extend around an outer surface of the aerosol-generating article received within the cavity; and
   a biasing mechanism configured to bias the cover element away from the open position and towards the closed position,
   wherein the biasing mechanism comprises a torsion spring, a first gear connected to the shaft portion of the cover element, and a second gear connected to the torsion spring, and
   wherein the first gear is engaged with the second gear and is configured to translate torque from the torsion spring to the shaft portion.

2. The aerosol-generating device according to claim 1, further comprising a first detent configured to retain the cover element in the open position.

3. The aerosol-generating device according to claim 2, further comprising a second detent configured to retain the cover element in the closed position.

4. The aerosol-generating device according to claim 1, further comprising a first mechanical stop configured to prevent rotation of the cover element beyond the closed position when the cover element is rotated from the open position to the closed position.

5. The aerosol-generating device according to claim 4, further comprising a second mechanical stop configured to prevent rotation of the cover element beyond the open position when the cover element is rotated from the closed position to the open position.

6. The aerosol-generating device according to claim 1, wherein the electrical heater further comprises an electrically insulating substrate and at least one resistive heating track on the electrically insulating substrate.

7. The aerosol-generating device according to claim 6, wherein the electrically insulating substrate comprises a flexible sheet.

8. The aerosol-generating device according to claim 1, wherein the aperture defines a first end of the cavity, wherein the cavity comprises a second end opposite the first end, and wherein the cavity has a maximum length between the first end of the cavity and the second end of the cavity of between 20 mm and 70 mm.

9. An aerosol-generating system, comprising an aerosol-generating device according to claim 1 and an aerosol-generating article, wherein the aerosol-generating article comprises an aerosol-forming substrate.

10. The aerosol-generating system according to claim 9, wherein the aerosol-generating article is sized such that, when the aerosol-generating article is fully inserted into the cavity of the aerosol-generating device, a portion of the aerosol-generating article extends out of the aerosol-generating device.

11. The aerosol-generating system according to claim 9, wherein the aerosol-generating article has a total length of between 40 mm and 50 mm.

\* \* \* \* \*